(12) United States Patent
Akcakir (10) Patent No.: US 7,460,240 B2
(45) Date of Patent: Dec. 2, 2008

(54) APPARATUS AND METHOD FOR DETECTING DEFORMABILITY OF CELLS USING SPATIALLY MODULATED OPTICAL FORCE MICROSCOPY

(75) Inventor: Osman Akcakir, Chicago, IL (US)

(73) Assignee: Arryx, Inc., Chicago, IL (US)

( * ) Notice: Subject to any disclaimer, the term of this patent is extended or adjusted under 35 U.S.C. 154(b) by 0 days.

(21) Appl. No.: 11/581,516

(22) Filed: Oct. 17, 2006

(65) Prior Publication Data

US 2007/0086919 A1    Apr. 19, 2007

Related U.S. Application Data

(60) Provisional application No. 60/726,620, filed on Oct. 17, 2005.

(51) Int. Cl.
*G01B 9/021* (2006.01)
(52) U.S. Cl. ..................................... 356/457
(58) Field of Classification Search ................ 356/496, 356/502, 503, 512, 515, 521
See application file for complete search history.

(56) References Cited

U.S. PATENT DOCUMENTS

| 5,689,109 | A  | * | 11/1997 | Schutze ........................ 250/251 |
| 6,055,106 | A  |   | 4/2000  | Grier et al. |
| 6,416,190 | B1 | * | 7/2002  | Grier et al. .................... 359/614 |
| 2004/0085540 | A1 | * | 5/2004 | Lapotko et al. ............. 356/432 |

OTHER PUBLICATIONS

Motility of live cancer cell quantified by Fourier phase microscopy, Popescu et al, SPIE-OSA vol. 5864, Aug. 2005, pp. 1-3.*

Guck, J., et al., "Optical Deformability as an Inherent Cell Marker for Testing Malignant Transformation and Metastatic Competence", Biophysical Journal, 88:3689-98, 2005.

Guck, J., et al., "The Optical Stretcher: A Novel Laser Tool to Micromanipulate Cells", Biophysical Journal, 2001, 81:767-84.

Lekka, M., et al., "Elasticity of normal and cancerous human bladder cells studied by scanning force microscopy", European Biophysics Journal, 1999, 28:312-6.

Popescu, G., et al., "Fourier phase microscopy for investigation of biological structures and dynamics", Optics Letters, 2004, 29(21):2503-5.

(Continued)

*Primary Examiner*—Michael A Lyons
(74) *Attorney, Agent, or Firm*—Jean C. Edwards, Esq.; Akerman Senterfitt (57) ABSTRACT

The present invention utilizes spatially modulated optical force microscopy (SMOFM) with single beam optical force probing capability or with a holographic optical trapping system capable of multi-beam optical force probing coupled to a microscope objective, to generate a probe beam(s) as a force probe to perturb the object that is adhered or resting on a surface, so that deformations of the object may subsequently be quantified. This quantification is performed by imaging a sequence of four phase shifted replicas of the image using a computer-controlled spatial light modulator, and calculating the pixel by pixel optical path-length using existing algorithms. The change in optical path lengths, and consequently the viscoelastic or elastic response elicited, is an indication of damage or disease when the objects are cells. In another embodiment, the optical deformability of the cells may be measured and correlated with measurements of cytoskeletal/structural protein expression.

57 Claims, 3 Drawing Sheets

OTHER PUBLICATIONS

Dufresne, E.R., et al. "Computer-Generated Holographic Optical Tweezers Arrays", Dept. of Physics et al., Oct. 27, 2000, 8.

Janmey, P.A., et al. "Viscoelastic Properties of Vimentin Compared with Other Filamentous Biopolymer Networks", The Journal of Cell Biology, 1991, 113(1), 155-160.

Jenmey, P.A., et al. "Dealing with mechanics: mechanisms of force transduction in cells", Trends in Biochemical Sciences, 2004, 29(7), 364-370.

Voros, Janos, "The Density and Refractive Index of Adsorbing Protein Layers", Biophysical Journal, 2004, 87, 553-561.

Kang, Y., et al. Epithelial-Mesenchymal Transitions: Twist in Development and Metastasis, Cell, 2004, 118, 277-279.

Thiery, Jean Paul, Epithelial-Mesenchymal Transitions in Tumour Progression, Nature Publishing Group, 2002, 2, 442-454.

Ghosh, S., et al. "Loss of Adhesion-Regulated Proteinase Production Is Correlated with Invasive . . . Cell Carcinoma", American Cancer Society, 2002, 2524-2533.

Yang, J., et al. "Twist, a Master Regulator of Morphogenesis, Plays an Essential Role in Tumor Metastasis", Cell, 2004, 117, 927-939.

Paszek, M.J., et al. "The Tension Mounts: Mechanics Meets Morphogenesis and Malignancy", Journal of Mammary Gland Biology and neoplasia, 2004, 9(4), 325-342.

MacKintosh, F.C., et al. "Elasticity of Semiflexible Biopolymer Networks", Physical Review Letters, 1995, 75(24), 4425-4429.

* cited by examiner

FIG. 1

APPARATUS AND METHOD FOR DETECTING DEFORMABILITY OF CELLS USING SPATIALLY MODULATED OPTICAL FORCE MICROSCOPY

The present invention claims priority from U.S. Provisional Patent Application No. 60/726,620, filed Oct. 17, 2005, the contents of which are herein incorporated by reference in its entirety.

BACKGROUND OF THE INVENTION

Diseases are often characterized by their unique molecular and/or genetic fingerprints. However, for many diseases, including cancer, this has yielded limited success; partly because there are many possible ways the molecular pathways in a cell may become pathological, there is much to learn.

Cancer is still a leading killer in the United States, despite decades of focused research activity on the problem. However cells, aside from being biochemical and genetic entities, are also mechanical entities which have physical properties such as elasticity. Diseases which effect the cytoskeletal protein network of cells (i.e. the structural integrity of the cell), including cancer, should naturally yield cells with altered mechanical properties (e.g. elasticity). This area of research is in still in its infancy, but recent research has successfully been able to distinguish cancerous cells from normal ones based on experimentally measuring an effective cellular elasticity (see ref. Guck et al.) by optical means.

Existing methods of applying forces to cells show that cancerous cells have increased deformability, as has been described in Guck, J., et al., "Optical Deformability as an Inherent Cell Marker for Testing Malignant Transformation and Metastatic Competence", Biophysical Journal 88:3689-98, 2005. It is known that photons, which carry momentum, are capable of exerting net forces on the center of mass of microscopic objects that have a refractive index different than the medium's (e.g., optical tweezers). Experiments done previously have shown that the surface forces that are generated can be much higher than the net forces, and are strong enough to deform biologically important objects, such as cells (see Guck, J., et al., "The Optical Stretcher: A Novel Laser Tool to Micromanipulate Cells", Biophysical Journal 81:767-84, (2001)). The Optical Stretcher of Guck et al. shows that among cells which otherwise look identical, the cancerous cells show significantly greater deformability when optical forces are applied.

Specifically, in the Optical Stretcher, two counter-propagating beams trap and stretch cells in suspension, one at a time. The magnitude of the stretching is recorded on a microscope mounted CCD camera and a measurement of the aspect ratio of the stretched cell (major axis over minor axis) yields an optical deformability parameter. The deformabilities measured are actually a convolution of the mechanical and optical properties (i.e., refractive index) of the cell, and so elastic moduli have to be inferred from these measurements based on knowledge of the optical properties, unlike the direct mechanical probe of a scanning force microscope (see Lekka, M., et al., "Elasticity of normal and cancerous human bladder cells studied by scanning force microscopy", European Biophysics Journal 28:312-6 (1999)). This is not a significant obstacle since for clinical purposes and most scientific purposes, statistical significance and robustness in a deformability measurement parameter is sufficient, and a rigorous calculation of the elastic moduli is not required.

Guck et al. have shown that the measured deformability correlates well with invasiveness, and that the optical deformability measure is related to the aspect ratios of the cells (major axis over minor axis).

The real limitation of the Optical Stretcher technique is, however, that only suspended cells may be measured. Unfortunately this is a non-physiological state for cells to be in, since they normally make cell-cell contacts and have a solid extracellular support (i.e., solid tissue). Since cells that do not have any surface to adhere to quickly lose their focal adhesion points and related stress fibers, there may be significant changes in the elastic properties of cells, compared to their in vivo properties, that are artifacts of the suspension conditions.

In other techniques to measure the elastic properties of cells, scanning force microscopy has been successfully applied to compare normal and cancerous cell elasticity on a surface, but this method suffers from two main difficulties: 1) the technique is exceeding slow (only several cells may be measured per day) making it difficult to envision translating into the clinical world, and 2) it is difficult to avoid mechanical contact with the sample, and so probe needle contamination is a real danger when measuring a series of cells.

Accordingly, a technique which can measure cells on a surface, which avoids damage to the cell, and which can speed up the technique to make it commercially viable, is needed.

SUMMARY OF THE INVENTION

One object of the present invention is to allow optical forces to be applied to adherent cells, and for the resultant surface deflections to a sensitive and quantifiable measurement of optical path links.

The spatially modulated optical force microscope (SMOFM) of the present invention will allow quantification of the deflections of the cell surface due to optically applied surface forces, to be detected with interferometric sensitivity (sub-nanometer sensitivity). Alternatively, SMOFM can be used to quantify the deflections of the cell surface due to non-optically applied surface forces (i.e., hydrodynamic, hydrostatic, electrostatic, magnetic, osmotic, mechanical, or inertial forces). The quantification is performed by imaging a sequence of four (4) phase shifted replicas of the image using a computer-controlled spatial light modulator, and calculating the pixel by pixel optical path-length using existing algorithms. The change in optical path lengths, and consequently shape changes, may be determined (assuming the refractive indices of each component fraction does not change).

Spatial Light Modulation of light is involved in up to two different ways in this invention. First, it is used in the detection of the path-length changes in the sample by spatially modulating the Fourier transform of the sample image that is illuminated with low-coherence light in transmission (imaging). Second, a separate spatial light modulator may be used to sculpt the laser light used for optically forcing object(s) in user-defined positions with user-defined intensities in the field of view (optical forcing). Each spatial light modulator in this embodiment modulates the light signal from a different source (Spatial Light Modulator (SLM) SLM1: imaging source, i.e. low-coherence diode), Spatial Light Modulator (SLM) SLM2: laser source for optical forcing).

Thus, with the present invention, optical deformability of any type of cell may be measured on the spatially modulated optical force microscope (SMOFM), so that diseased cells, including cancer cells, that have a unique optical deformability signature may be identified. In addition to being used as a diagnostic tool, the spatial light modulated force microscope may also be used as an investigative tool to understand the causes of any change in optical deformability due to a particular diseased cell state. Optical deformability of such cells may be correlated with structural protein expression levels and patterns, for example, allowing the spatially modulated force microscope to uncover the molecular origins for the changes in the viscoelastic responses of cells brought on by disease.

The apparatus of the present invention is optically based, so it has the advantages of being a quick and sterile measurement platform. In contrast to the prior art, the objects or cells to be probed in the present invention may be adhering to a surface (i.e., microscope cover slip surface), and so are able to retain their naturally present focal adhesions and stress fibers.

The present detection technique (using spatially modulated optical microscopy) is a much more sensitive technique for the detection of deformation, with sub-nanometer level sensitivity, compared to that of prior art methods. The greater sensitivity of the present invention has two important advantages: 1) a greater dynamic range of elastic responses may be probed, and 2) detectable deformations may be achieved at lower laser powers. The second advantage is an important consideration for parallelization.

In another embodiment, the optical deformability of the normal and diseased cells may be measured and correlated with measurements of cytoskeletal/structural protein expression. Protein expression may be determined by fluorescently tagging the targeted protein, and collecting fluorescence images for example.

In this way the optical force microscopy apparatus of the present invention is a valuable tool for correlating molecular and genetic patterns in cells with a mechanical measurement of deformability, adding a new dimension to the characterization of cancerous phenotypes. The present invention also provides a basis for a cancer screening assay based on a deformability measurement parameter.

There has thus been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention is related to an optical force measurement device that can apply optically based forces and sensitively detect the resulting deformations in objects, such as cells, while the objects rest on or adhere to a surface, rather than being in suspension as in previous applications.

In particular, in one embodiment, the present invention measures deformations in the object as a function of an applied optical force, using holographic optical trapping technology, for example, to direct optical forces to potentially many regions of interest simultaneously.

In another embodiment, the present invention measures deformations in the object using a quantitative phase contrast microscopy technique—e.g. spatially modulated optical force microscopy (SMOFM).

In a preferred embodiment, the present invention utilizes spatially modulated optical force microscopy (SMOFM) with single beam optical force probing capability or with a holographic optical trapping system capable of multi-beam optical force probing coupled to a microscope objective, to generate a probe beam(s) as a force probe to perturb the object that is adhered or resting on a surface, so that deformations of the object(s) may subsequently be measured.

The present invention allows objects to be measured without being in suspension, in contrast to prior art techniques. In fact, the object being measured in the present invention, may be any type of adherent cell, and optical techniques are used to determine whether the cell is a normal or a cancerous cell. Other cell types (e.g., stem cells) or cell states (e.g., disease states) may also be detected and/or characterized by optical deformability provided that the target cell type or cell state has a characteristic elastic or viscoelastic response to the optically based force probe.

The optically generated surface forces that generate the cellular deflections of interest is due to the conservation of photon momentum as it traverses media of different refractive indices. When a photon in media 1 with refractive index $n_1$ crosses over into media 2 with refractive index $n_2$, the photon's momentum changes from $n_1 E/c$ to $n_2(1-R)E/c$, where E is the photon energy and R is the reflectivity given by the Fresnel formulas ($R \sim 10^{-3}$). In addition there is a reflected component whose photon momentum is $n_1 RE/c$. For momentum conservation a momentum on the surface is picked up, given by $\Delta p$.

The surface thus, experiences a force $F = \Delta p / \Delta t$. In this way the surface force deflects the surface away from the denser medium, and thereby increases the optical path-length of the denser medium along the incident axis. By measuring the optical path-length shifts for different samples, their optical deformabilities may be compared.

Thus, the extent of the surface deflections (i.e., strain) of the objects are a function of the viscoelastic properties of the material. Comparing the response of two (2) objects with identical optical characteristics under equivalent illumination conditions, allows a comparison of their viscoelastic response.

In the present invention, measurement is performed by quantifying the deflections of the object's surface due to the optically applied surface forces by imaging a sequence of phase-shifted replicas of the image of the object, and calculating the pixel by pixel optical path-length using an algorithm. The optical deformability observable contains a measure of the shape change (e.g., fractional change in optical path-length) at a given incident intensity (and beam profile). The optical path-length is defined as the true physical length of an object that the beam traverses, L, multiplied by its refractive index, n (i.e. optical path-length=nL). Thus, by measuring the optical path-length shifts for the object, such as a cancerous cell, and comparing it with that of other objects (i.e., non-cancerous cells), the optical deformabilities may be obtained, and carcinoma diagnosed.

In particular, detection of oral squamous cell carcinoma (OSCC) may be determined by the present technique. The resulting cancerous epithelial cells (which are adherent) are much more common than cancers derived from stromal cells like fibroblasts (i.e., sarcomas), and are prime candidates for the detection of carcinomas by this technique, which can interrogate such cells.

However, the present technique is also applicable to test any cell for any type of carcinoma (i.e., cancer derived from any type of epithelium of any organ such as breast, prostate, etc.).

Specifically, in the present invention, the objects (for example, cells—either provided from a patient or cultured cell lines) are formed on a monolayer on the surface of a substrate, and when light is applied to the objects, the photons will traverse the material of the indices $n_1$ (cell media), $n_2$ (cell) and $n_3$ (substrate). It should be appreciated that $n_2 > n_3$ otherwise the cells will come off the surface due to surface forces (i.e., otherwise the surface of the cell adjacent to the substrate will be pushed away from the substrate, causing detachment).

This relation is not satisfied for typical substrates such as glass or plastic but there exists a special class of amorphous fluoropolymers (i.e., Teflon® AF, Dupont) that have indices of refraction comparable to or less than water, and are transparent. Cells on a substrate of this type of amorphous fluoropolymer (which is chemically inert), will not come off the surface by the optical surface forces exerted on the cell at this boundary.

In the event that cells are not able to adhere onto a fluoropolymer substrate surface directly, the surface may be coated with one of a variety of proteins, such as laminin-5, collagen I or fibronectin, to allow the cells to attach. The cells may be measured for normal and cancerous (i.e., OSCC, oral squamous cell carcinoma) epithelial cells.

In one embodiment, the optical deformability (a measure of cellular elasticity/viscoelasticity) of the cells is correlated with measurements of cytoskeletal protein expression (for example, fluorescence), and correlated with measurements of invasiveness, to determine if carcinomas are present.

Figure 1:
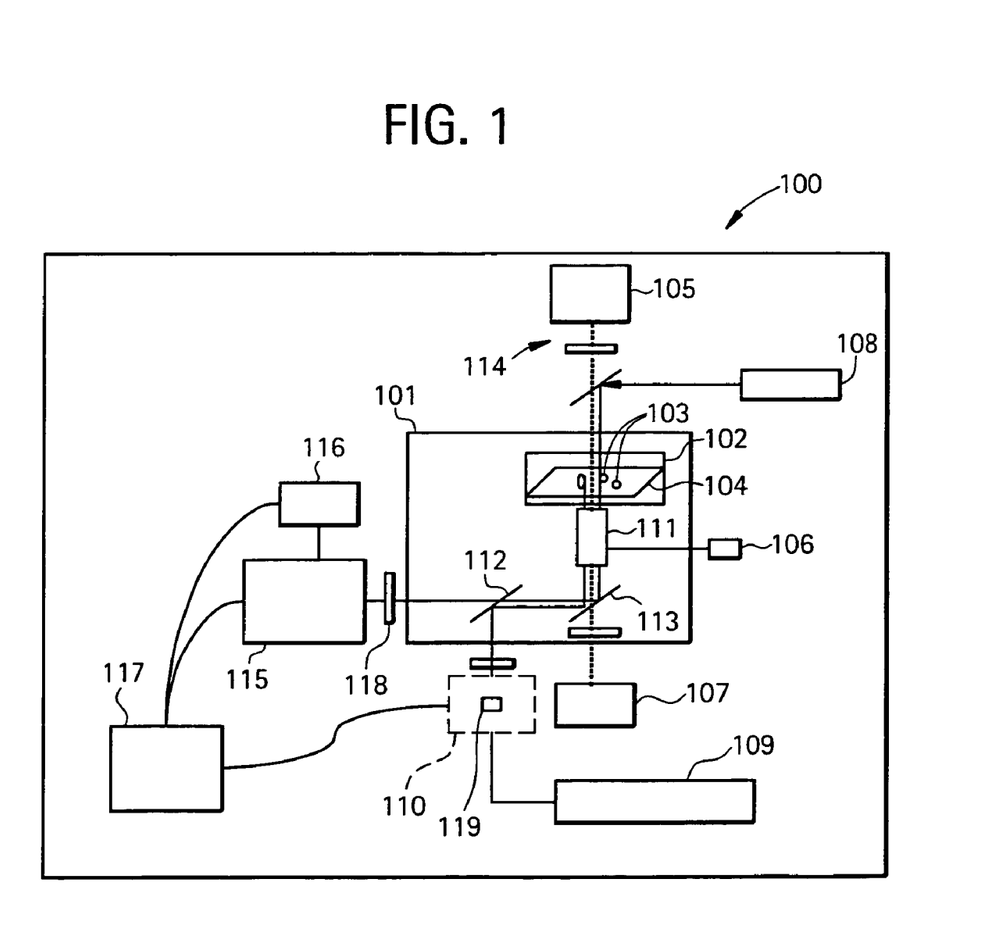
FIG. 1 shows an optical force measurement apparatus according to one embodiment consistent with the present invention.

Specifically, in one embodiment consistent with the present invention, FIG. 1 shows a schematic of an apparatus 100 for performing spatially modulated optical force microscopy (SMOFM) on adherent cells using holographic optical trapping technology.

However, one of ordinary skill in the art would know that the present invention may be performed on adherent cells using spatially modulated optical force microscopy without the use of holographic optical trapping technology, or without the use of optically applied forces. Alternatively, if holographic optical trapping technology is used for applying optical forces, the present invention may be implemented without Fourier phase techniques as outlined in the present invention, and instead, utilize other quantitative phase microscopy techniques.

The laser-coupled spatially modulated optical force microscope (SMOFM) apparatus 100 of the present invention utilizes an inverted Nikon TE200 microscope 101, for example, with a temperature controlled sample stage 102 as the platform. The objects (i.e., adherent cells) 103, which are grown on an amorphous fluropolymer-coated cover glass or slide 104, or an amorphous fluoropolymer-coated cover glass or slide 104 coated with a protein as described above, for example, may be placed on the sample stage 102 (controlled to 37° C., for example).

In one embodiment, a lamp 105 of sufficient wattage is used to illuminate the objects 103 on the microscope slide 105, such that the objects 103 can be adequately viewed through an eyepiece 106 of the microscope 101, and through an imaging mechanism, such as a camera (CCD 107). This illumination by the lamp 105 may be eliminated, if so desired.

A low-coherence source, such as a superluminescent diode 108, is used for imaging (i.e., an OLSLD-820-HP1, Laser 2000, with a center wavelength of 820 nm, and 14 nm bandwidth). The superluminescent diode 108 provides wide-field illumination of the object 103 on the slide 104 with a narrow bandwidth and low coherence length in transmission, for the purpose of measuring the path length differences over the field of view—and is particularly suitable for spatial light modulated force microscopy techniques.

However, instead of a superluminescent diode 108, an alternative coherent light source, such as a suitable laser, may be used, for any of the quantitative phase microscopy techniques, including spatial light modulated force microscopy. The light from the superluminescent diode 108 is suitably collimated at the object plane, using an objective lens 111, such that the diameter of the beam overfills the viewing area.

For a spatially modulated optical force microscope 101 with only one probe beam, the optical force laser (i.e., 1064 nm, V106C, Spectra-Physics) 109 is coupled into an objective 111 via the dichroic mirror 113 with a free-space beam or with a fiber optically-coupled beam. This beam is brought into focus at the back aperture plane of the objective 111 to generate a collimated beam from the objective lens 111. The laser 109 output power can be controlled by a calibrated, computer-controlled laser attenuator 119 (i.e., OZ Optics), placed at the output aperture of the laser 109, in order to control the magnitude of the optical force applied to the objects 103.

In order to provide a means to measure optical path lengths of a number of objects 103 on the slide 104 in parallel, a holographic optical trapping (HOT) apparatus 110 (see U.S. Pat. No. 6,055,106, to Grier et al., for example, which is herein incorporated by reference), is applied as a light source. The HOT light source which illuminates the objects 103 is a laser 109 (e.g., a 1064 nm, V106C, Spectra-Physics laser) which is used to apply an optically generated force.

For a spatially modulated optical force microscope 101 with a user-definable number of traps that can be dynamically changed, the HOT apparatus 110 may be utilized to modify the wavefront from the optical force laser 109 to apply points of light to locations of interest (e.g., where objects 103 or cells are present in the field of view).

Specifically, the HOT apparatus 110 (see FIG. 2) includes a collimated laser beam 201 which is shaped by a diffractive optical element 202 and transferred to a back aperture of an objective lens 203 via, for example, telescope lenses 204, 205 and dichroic mirror 206, and focused into a plurality of optical traps 207, which are illuminated by beam 208. The point B' is conjugate to B. Note, however, that telescope lenses 204, 205 may be eliminated from the apparatus, if desired.

Figure 2:
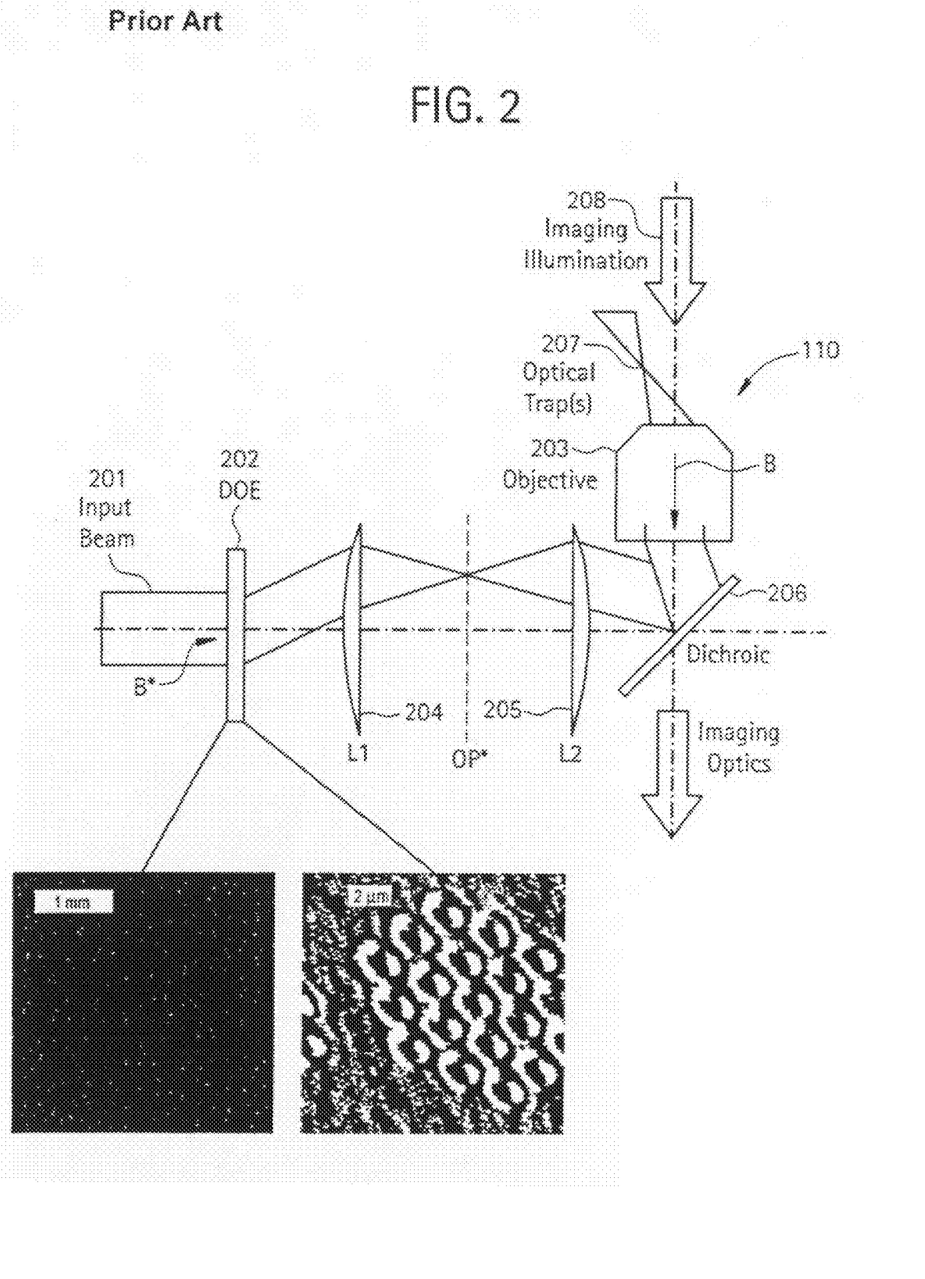
FIG. 2 shows an exemplary holographic optical trapping system which is a part of the apparatus of FIG. 1, according to one embodiment consistent with the present invention.

In FIG. 1, some elements of the HOT apparatus 110 of FIG. 2 are shown. For example, the objective lens 203 is a microscope objective lens 111, which focuses the light beam 208 to form optical traps 207 which affect the objects 103 on the slide 104.

Thus, objects 103 (e.g., cells) on the slide 104 may have pressure applied to them by using the HOT apparatus 110 as a high intensity source (i.e., laser 109, for optical probing). This pressure is directed to each of the objects 103 on the slide 104.

Further, to perform the measurement of the optical path lengths of the objects 103 or cells more efficiently, holographic optical techniques are used to parallelize the optical force probes. By using the computer-controlled SLM 115 to control the phase of a single laser's 109 wave-front, it is possible to position and apply multiple optical force probes in a field of view simultaneously.

Further, since the detection method employing the spatially modulated optical force microscopy technique measures the optical path-lengths for the whole field of view at once, pixel by pixel, the present invention will be easily scalable to measure many objects 103 or cells in parallel (also, with automation, if desired). Thus, many objects 103 or points within the object sample 104 (e.g., cells) may be probed simultaneously by creating many probe beams (beamlets) with a single source (using HOT 110, for example).

In the present invention, illumination of the objects 103 is achieved by a bandpass filter 114 which is placed in front of the lamp 105, and which allows a visible band of light to emerge from the lamp 105 through to the viewing camera (CCD) 107, and to exclude light from the other two light sources (i.e., the laser 109 and the superluminescent diode 108). As stated above, this visible band of light is for viewing by the user and may be omitted from the apparatus, if desired.

Figure 3:
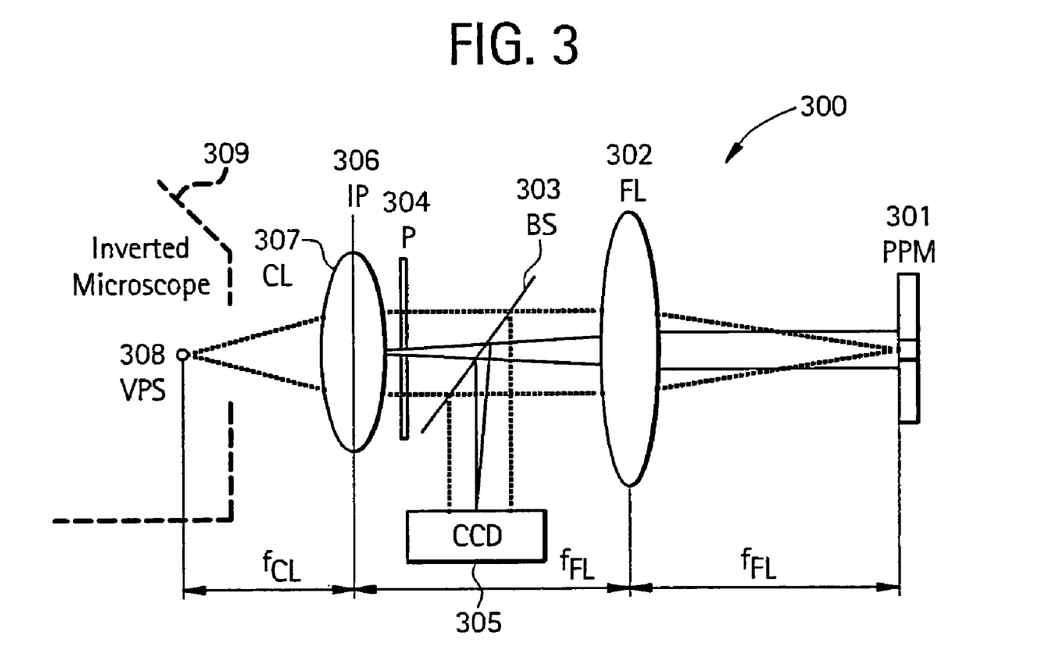
FIG. 3 shows a diagram of optical components necessary to perform spatial light modulated optical force microscopy, which is part of the apparatus of FIG. 1, according to one embodiment consistent with the present invention.

The transmitted light from the superluminescent diode 108 is imaged as a superposition of the unmodified image plus a phase shifted version of the image, and is accomplished by a spatial light modulator (SLM) 115, also known as a programmable phase modulator (PPM) (i.e., a X8267 Hamamatsu Photonics, K.K.), which is part of the SMOFM 300 shown in FIG. 3. The transmitted light passes through bandpass filter 118 which allows only light from the superluminescent diode 108 to be imaged on imaging mechanism or CCD 116, and blocks laser 109 light from reaching the CCD 116.

A computer-controlled interface 117 integrates the SLM 115, CCD 116 image acquisition, HOT 110 and laser attenuator 109 control (i.e., from OZ Optics), and image processing necessary for position dependent optical path length calculations, and may have software written in a graphical programming language.

In the present invention, measurements of the optical deformations of the object 103 are performed using spatially modulated optical force microscopy (SMOFM). As stated above, SMOFM quantitatively measures the optical path length changes as a result of the optical forces applied by the HOT 110.

The present technique involves the introduction of a second light source (i.e., the low coherence superluminescent diode 108), which is fiber collimated after emerging from a single mode fiber (ensuring spatial coherence). The superluminescent diode 108 provides plane wave illumination of the objects 103 with spatially coherent light, and the low temporal coherence of the light from diode 108 prevents problematic reflection artifacts during detection. A Fourier transform of the image field is projected onto the surface of the SLM 115. This image is then back transformed to form a real image of the objects 103 on CCD 116. Without any modulation on the SLM 115, the original image is reconstructed on the CCD 116. By modulating only the k=0 component of the SLM 115 (given by pixels in the central spot), the phase of the DC level of the image may be modulated independently of the spatially varying component 115.

The present technique includes stepping the phase of the DC component of the image through four (4) phase shifts (of $\pi/2$ each) and capturing the resultant four (4) CCD images which store the interference of the DC and spatially varying fields of the image, pixel by pixel.

Existing algorithms (see equations [1] to [4] below) are used to obtain the phase difference between the DC field and spatially varying field, pixel by pixel, using the four (4) images obtained. This phase-shift is equivalent to the optical path-length shift undergone by the light at that pixel location.

By the mathematical relationships above, the information from four (4) phase shifted images can be expressed as a phase distribution of the E field. And by comparing the phase distribution before and after optical forcing, the desired pixel by pixel optical path-length shift information is acquired.

For example, the electric field in the image plane is $E = E_0 + E_1$, where the total field E is split into a spatially non-varying field (DC component) $E_0$ and a spatially varying component $E_1$. The intensity measured on the CCD 116 for each of the four (4) phase shifts (n=0, 1, 2, 3) is given by:

$$I(x,y;n) = |E_0|^2 + |E_1(x,y)|^2 + 2|E_0||E_1(x,y)|\cos[\Delta\phi(x,y) + n\pi/2], \quad [1]$$

where n=0, 1, 2, 3.

$\Delta\phi(x,y)$ is the phase difference between $E_0$ and $E_1(x,y)$ at pixel position (x,y), and is given by:

$$\tan(\Delta\phi(x,y)) = [I(3) - I(1)]/[I(0) - I(2)]. \quad [2]$$

The phase distribution of the E field, $\phi(x,y)$ is given by, $$\phi(x,y) = \tan^{-1}\{\beta(x,y)\sin[\Delta\phi(x,y)]/(1+\beta(x,y)\cos[\Delta\phi(x,y)])\}, \quad [3]$$

and $$\beta(x,y) = |E_1(x,y)|/|E_0| = \gamma[I(x,y;0) - I(x,y;2) + I(x,y;3) - I(x,y;1)]/[\sin[\Delta\phi(x,y)] + \cos[\Delta\phi(x,y)]], \quad [4]$$

where $\gamma = 1/4|E_0|^2$.

By these existing mathematical relationships (see Popescu, G., et al., "Fourier phase microscopy for investigation of biological structures and dynamics", Optics Letters 29(21): 2503-5 (2004)), the information from the four (4) phase shifted images can be expressed as a phase distribution of the E field. By comparing the phase distribution before and after optical forcing, the desired pixel by pixel optical path-length shift information is acquired.

Accordingly, in the present invention, the image signal from the superluminescent diode 108 is modified by first placing a correcting lens (CL) 307 (see FIG. 3) at the focal plane of the image (CL 307 may be selected to have a focal length equal to the image plane (IP) 306/virtual point source (VPS) 308 distance). Then the image is Fourier transformed using a Fourier lens 302 (e.g., focal length of 50 cm), using standard 4-f geometry, onto the surface of the SLM or PPM 301 (SLM 115 in FIG. 1).

The spatial light modulator SLM 115 (i.e., programmable phase modulator (PPM) (i.e., a X8267 Hamamatsu Photonics, K.K.)) may be an individually addressable 2-dimensional liquid crystal array, which is designed to have independent phase control between 0 to $2\pi$ with at least 8 bit resolution for each pixel. This phase control is possible by selecting the polarization of the incident light to match the direction of the molecular axis of the liquid crystal by inserting a polarizer P 304. The phase modulated image that is reflected off the SLM 301 is imaged onto a CCD camera 305 (CCD 116 in FIG. 1) by reflection off a beam splitter (BS) 303 onto the CCD 116.

Thus, the measurement of each object 103 may include 1) measurement of the optical path-length of the object 103 when no optical force is present (yielding optical path-length L), and 2) measurement of the optical path-length of the object 103 after an optical force is applied (yielding optical path-length L'). The technique of the present invention will yield a measurement of the optical deformability (i.e., strain, (L'-L)/L) which can be compared to the optical deformability of other objects to determine if the elasticity of the cells provides a determination of carcinoma. Thus, the duration and magnitude of the applied optical force will determine whether an elastic and/or viscoelastic response from the object 103 is elicited, and whether the magnitude of the elastic and/or viscoelastic response is indicative of carcinoma.

In another embodiment, the optical deformability of the objects or cells may be measured and correlated with measurements of cytoskeletal/structural protein expression (via fluorescent microscopy of cells). For example, there are many methods known in the art for using fluorescence to image and quantify protein expression using immunolocalization (see Imai, K., et al., "Immunolocalization of desmoglein and intermediate filaments in human oral squamous cell carcinomas", Head Neck 17:204-12 (1995)).

Further, it has been shown that cancerous oral epithelial cells express vimentin. There have also been reports suggesting that vimentin expression is detectable even before the tumor cells exhibit a mesenchymal morphology, which makes the hypothesized vimentin mediated change in cellular deformability a potentially desirable diagnostic marker.

To correlate protein expression through immunolocalization, one could incubate cells with specific antibodies (i.e., anti-vimentin), wash the cells, then incubate the cells with fluorescently labeled secondary antibodies, such as Alexa Fluor 594 secondary antibody, wash and finally prepare the cells for fluorescent image analysis in combination with SMOFM.

In a similar way, the technique of the present invention may be used to correlate any desirable protein expression marker with the optical deformability of cells.

Thus, the apparatus of the present invention allows optical forces to be applied to adherent cells, for example, and their resultant surface deflections may be sensitively and quantifiably measured. The spatially modulated optical force microscopy component of the present invention will allow quantification of the deflections of the cell surface due to optically applied surface forces, to be detected with interferometric sensitivity (sub-nanometer sensitivity). The change in optical path length changes, and consequently shape changes, may be determined, so that diseased cells, including cancer cells, that have a unique optical deformability signature may be identified.

Thus, the optical force microscopy apparatus of the present invention is a valuable tool for correlating molecular and genetic patterns in cells which show a mechanical measurement of deformability, adding a new dimension to the characterization of cancerous phenotypes. The present invention also provides a basis for a cancer screening assay based on a deformability measurement parameter.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. An apparatus for detecting deformation in a plurality of objects, comprising:

a first light source comprising a laser apparatus for emitting a laser beam which applies an optically generated force to each of the objects;

a second light source which is a low-coherence light source and which provides wide-field illumination of the objects;

a support mechanism to support the plurality of objects, the objects which are illuminated by said low-coherence light source to form images of the objects;

a Fourier lens for Fourier transforming said images of the objects disposed on the support mechanism after illumination from the low-coherence light source;

a spatial light modulator which receives the images of the objects from the Fourier lens and phase shifts said images in a predetermined manner; and a first imaging mechanism which detects changes in optical path lengths of the objects based on said phase shifts due to said optically generated forces, and which yields a measurement of optical deformability thereof.

2. The apparatus according to claim 1, wherein said laser is one element of
a holographic optical trapping mechanism.

3. The apparatus according to claim 2, wherein the objects are adherent cells.

4. The apparatus according to claim 3, further comprising:

a third light source comprising a lamp which illuminates the objects in addition to said low-coherence light source; and a first bandpass filter disposed downstream from said lamp and upstream from said support mechanism, which allows a band of light to emerge from said first bandpass filter, to illuminate the objects for said first imaging mechanism and to exclude light from said laser and said low-coherence light source.

5. The apparatus according to claim 4, wherein said spatial light modulator is an element in a spatially modulated optical force microscopy mechanism.

6. The apparatus according to claim 5, wherein said holographic optical trapping mechanism includes a microscope containing an objective lens;

wherein said microscope further comprises an amorphous fluorpolymer-coated cover glass disposed on said support mechanism; and wherein said cells are grown on said amorphous fluorpolymer-coated cover glass.

7. The apparatus according to claim 6, wherein said holographic optical trapping mechanism further comprises an objective lens, and a light beam generated from said laser of said holographic optical trapping mechanism is brought into focus at a back aperture of said objective lens.

8. The apparatus according to claim 6, further comprising:
a computer-controlled laser attenuator disposed at an output aperture of said laser, which controls a magnitude of power of said laser and said optically generated forces applied to said cells.

9. The apparatus according to claim 8, wherein said holographic optical trapping mechanism modifies a wavefront from said laser to apply beamlets to the cells to impart optical forces onto the cells.

10. The apparatus according to claim 9, wherein said holographic optical trapping mechanism further comprises a diffractive optical element, and said beamlets are shaped by said diffractive optical element.

11. The apparatus according to claim 9, wherein said beamlets act as optical force probes which apply pressure to the cells simultaneously.

12. The apparatus according to claim 6, wherein said cover glass is coated with a protein.

13. The apparatus according to claim 5, wherein said spatially modulated optical force microscopy mechanism further comprises:
a second imaging mechanism which images said phase shifts of each of the cells;
wherein transmitted light from said low-coherence light source is imaged as a superposition of unmodified images of the cells plus phase shifts of said images of the cells, by said spatial light modulator using said second imaging mechanism.

14. The apparatus according to claim 13, further comprising:
a computer-controlled interface which integrates said spatial light modulator, said second imaging mechanism, said holographic optical trapping mechanism, and said computer-controlled laser attenuator.

15. The apparatus according to claim 14, further comprising:
a second bandpass filter disposed in front of said spatial light modulator, and which allows only light from said low-coherence light source to be imaged on said second imaging mechanism.

16. The apparatus according to claim 13, wherein a phase of a DC component of said unmodified image is stepped through four phase shifts by said spatial light modulator and said resulting four phase-shifted images store an interference of said DC and spatially varying fields of said phase-shifted images.

17. The apparatus according to claim 16, wherein each of said phase-shifts is equivalent to an optical path-length shift undergone by light at that pixel location.

18. The apparatus according to claim 13, wherein said spatially modulated optical force microscopy mechanism further comprises:
a correcting lens disposed at a focal plane of said image.

19. The apparatus according to claim 18, wherein said spatial light modulator is an individually addressable two-dimensional liquid crystal array, which has an independent phase control between 0 to $2\pi$ with at least 8 bit resolution for each pixel.

20. The apparatus according to claim 19, wherein said spatially modulated optical force microscopy mechanism further comprises:
a polarizer disposed downstream of said correcting lens, and upstream from said Fourier lens;
wherein incident light on said liquid crystal array is polarized to match a direction of a molecular axis of said liquid crystal array.

21. The apparatus according to claim 20, wherein said spatially modulated optical force microscopy mechanism further comprises:
a beam splitter disposed downstream of said polarizer and upstream from said Fourier lens;
wherein a phase modulated image that is reflected off said spatial light modulator is imaged onto said second imaging mechanism by reflection off said beam splitter.

22. The apparatus according to claim 1, wherein said low-coherence light source is a superluminescent diode.

23. The apparatus according to claim 1, wherein said low-coherence light source is a laser.

24. The apparatus according to claim 1 wherein said spatial light modulator is a programmable phase modulator.

25. The apparatus according to claim 1, wherein a measurement of said optical deformability includes measuring a strain of the objects.

26. The apparatus according to claim 25, wherein said strain is defined as $(L'-L)/L$, where L is a measurement of said optical path-length of each of the objects when no optical force is present, and L' is a measurement of said optical path-length of each of the objects after said optically generated forces are applied.

27. The apparatus according to claim 25, wherein said measurement of optical deformability is compared to an optical deformability of other previously measured objects to determine if a change in a viscoelasticity or an elasticity of the objects provides a determination of disease or damage.

28. The apparatus according to claim 27, wherein said optical deformability of said objects is measured and correlated with measurements of cyboskeletal/structural protein expression.

29. The apparatus according to claim 28, wherein said protein is vimentin.

30. The apparatus according to claim 1, wherein said optically generated forces which are applied to the cells to measure the deformability, are non-optical.

31. A method of detecting a measurement of deformability in a plurality of cells, comprising:
applying optically generated forces to the cells using a laser which generates a laser beam;
illuminating the cells on a substrate using a low-coherence light source which provides wide-field illumination of the cells and forms images of the cells;
transforming said images of the cells disposed on the substrate after illumination from the low-coherence light source, using a Fourier lens;
receiving said images on a spatial light modulator which phase shifts said images in a predetermined manner;
determining differences in optical path lengths of each of the cells based on said phase shifts due to said optically generated forces; and
determining optical deformability of the cells by comparing said differences with optical path lengths of other non-deformed cells.

32. The method according to claim 31, wherein the laser is part of
a holographic optical trapping mechanism.

33. The method according to claim 32, further comprising:
focusing a light beam generated from said laser of said holographic optical trapping mechanism, at a back aperture of an objective lens of said holographic optical trapping mechanism, in order to apply said optically generated forces to the cells.

34. The method according to claim 33, further comprising:
controlling a magnitude of power of said laser and an optical force applied to said cells with a computer-controlled laser attenuator disposed at an output aperture of said laser.

35. The method according to claim 34, further comprising:
modifying a wavefront from said laser using said holographic optical trapping mechanism to apply beamlets to said cells.

36. The method according to claim 35, wherein said beamlets are shaped by a diffractive optical element of said holographic optical trapping mechanism.

37. The method according to claim 36, wherein said step of applying optically generated forces further comprises:
applying pressure to said cells simultaneously by using said beamlets as optical force probes.

38. The method according to claim 37, further comprising:
imaging phase shifts of each of said cells using a second imaging mechanism; and
imaging transmitted light from said low-coherence light source as a superposition of unmodified images of said cells plus phase shifts of said images of said cells, using said second imaging mechanism.

39. The method according to claim 38, wherein said spatial light modulator is a programmable phase modulator.

40. The method according to claim 38, further comprising:
imaging light from said low-coherence light source onto said second imaging mechanism using a second bandpass filter disposed in front of said spatial light modulator.

41. The method according to claim 40, further comprising:
integrating said spatial light modulator which is part of a spatially modulated optical force microscopy mechanism, said second imaging mechanism, said holographic optical trapping mechanism, and said computer-controlled laser attenuator of said holographic optical trapping mechanism, using a computer-controlled interface.

42. The method according to claim 41, wherein said spatial light modulator is an individually addressable two-dimensional liquid crystal array, which has an independent phase control between 0 to $2\pi$ with at least 8 bit resolution for each pixel.

43. The method according to claim 42, further comprising:
polarizing light incident on said liquid crystal array using a polarizer disposed in front of said Fourier lens, to match a direction of a molecular axis of said liquid crystal array.

44. The method according to claim 43, further comprising:
imaging a phase modulated image reflected off said spatial light modulator onto said second imaging mechanism by reflection off a beam splitter.

45. The method according to claim 40, further comprising:
quantitatively measuring said differences in said optical path lengths of the cells as a result of said optically generated forces applied by said laser of said holographic optical trapping mechanism.

46. The method according to claim 38, wherein said imaging step further comprises:
stepping through four phase shifts of a phase of a DC component of said unmodified images of the cells;
wherein said resulting four phase-shifted images of the cells store an interference of said DC and spatially varying fields of said phase-shifted images of the cells.

47. The method according to claim 31, wherein the cells are adherent cells.

48. The method according to claim 47, further comprising:
growing said cells on an amorphous fluoropolymer-coated cover glass prior to the illuminating step, for better measurement of the cells.

49. The method according to claim 48, wherein the cover glass is coated with a protein.

50. The method according to claim 31, wherein said illuminating step comprises:
illuminating the cells with a lamp;
allowing a band of light to illuminate the cells, using a first bandpass filter, which illuminates the cells for a first imaging mechanism and which excludes light from said laser and said low-coherence light source; and
viewing the illuminated cells with said first imaging mechanism.

51. The method according to claim 31, wherein said low-coherence light source is a superluminescent diode.

52. The method according to claim 31, wherein said low-coherence light source is a laser.

53. The method according to claim 31, further comprising:
measuring a strain of the cells to determine a measurement of said optical deformability.

54. The method according to claim 53, wherein said strain is defined as $(L'-L)/L$, where L is a measurement of said optical path-length of one of said cells when no optical force is present, and L' is a measurement of said optical path-length of one of said cells after optically generated forces are applied.

55. The method according to claim 54, further comprising:
comparing said measurement of optical deformability to an optical deformability of said non-deformed cells to determine whether a viscoelasticity or an elasticity of the imaged cells provides a determination of disease or damage.

56. The method according to claim 55, further comprising:
measuring and correlating said optical deformability of the imaged cells with measurements of cytoskeletal/structural protein expression, to determine whether said expression is a determination of disease or damage.

57. The method according to claim 56, wherein said protein is vimentin.

* * * * *